(12) United States Patent
Kristyanne et al.

(10) Patent No.: US 6,504,021 B2
(45) Date of Patent: Jan. 7, 2003

(54) ION EXCHANGE METHOD FOR DNA PURIFICATION

(75) Inventors: Eva Kristyanne, Rockville, MD (US); Reyes Candau, Olney, MD (US); John L. Seed, Ellicott City, MD (US)

(73) Assignee: Edge Biosystems, Inc., Gaithersburg, MD (US)

( * ) Notice: Subject to any disclaimer, the term of this patent is extended or adjusted under 35 U.S.C. 154(b) by 0 days.

(21) Appl. No.: 09/898,473

(22) Filed: Jul. 5, 2001

(65) Prior Publication Data

US 2002/0042506 A1 Apr. 11, 2002

Related U.S. Application Data

(60) Provisional application No. 60/216,355, filed on Jul. 5, 2000.

(51) Int. Cl.[7] .............................. C07H 21/04; C07H 1/06

(52) U.S. Cl. ....................... 536/23.1; 536/127; 521/30

(58) Field of Search ............................ 521/30; 536/127, 536/128, 23.1

(56) References Cited

PUBLICATIONS

Spicer et al., "A Fully Automated Process Using a Magnetic Particle Based Kit for Removal of Dye Terminators from Sequencing Reactions", *JALA*, vol. 6, No. 2, pp. 63–66 (May 2001).

*Primary Examiner*—Remy Yucel
*Assistant Examiner*—Celine Qian
(74) *Attorney, Agent, or Firm*—Banner & Witcoff, Ltd.

(57) ABSTRACT

A method and materials are described for purification of DNA using ion exchange resins. This ion exchange method provides the means to remove salts and low molecular weight contaminants from DNA in solution without binding or removing the DNA of interest.

26 Claims, No Drawings

ION EXCHANGE METHOD FOR DNA PURIFICATION

This application claims the benefit of provisional application serial No. 60/216,355, filed Jul. 5, 2000, the disclosure of which is expressly incorporated herein.

FIELD OF THE INVENTION

The field of the invention is methods for purification of DNA.

BACKGROUND TO THE INVENTION

DNA purification technologies fall into two general categories, methods that involve selective adsorption of DNA to a substrate, and methods that involve removal of contaminants from soluble DNA. The latter was one of the first technologies used for the purification of DNA and involved primarily the extraction of DNA with liquid phenol, followed by precipitation with salt and ethanol (Maniatis, T., et al., Eds. Molecular Cloning, Cold Spring Harbor Lab., 90–91, 1982.). Additional variations on this approach have been developed including salting-out techniques that use protein precipitants as well as solid phase technologies that adsorb biological contaminants. These are disclosed in U.S. Pat. No. 5,561,064 and U.S. Pat. No. 4,923,978. The phenolic technology, while still in use, is time-consuming, the reagent is toxic and environmentally damaging and the technology is difficult to automate. The aforementioned variations on this technique tend to be expensive and time-consuming. For these and other reasons, selective adsorption of DNA to a substrate has become the most commonly used technology in the last decade. In the presence of chaotropic agents, DNA can be adsorbed to a variety of silicates as disclosed by Vogelstein, B., et al., (Proc. Natl. Acad. Sci. USA 76:615–619, Febuary 1979) and in U.S. Pat. Nos. 5,075,430 and 5,234,809 as well as in some non-silicate materials (U.S. Pat. No. 5,705,628). More recently, silicates and other silicon-containing substances have been developed that have reduced dependency on salt, as disclosed in U.S. Pat. Nos. 5,523,392 and 5,525,319). Once adsorbed, soluble contaminants are physically removed and co-adsorbed contaminants are removed by selective washing. The purified DNA is then eluted from the substrate with water or a weak buffer. DNA may also be purified by adsorption to ion exchange resins. DNA is a negatively charged molecule that binds when contacted with cationic resins. U.S. Pat. No. 5,057,426 discloses a method for purifying DNA with a porous cationic resin matrix. In this method, the DNA binds to the matrix and soluble contaminants are physically removed. Co-adsorbed contaminants are removed by selective washing with salt. Purified DNA is subsequently desorbed from the resin by high concentrations of salt. Due to the high density of negative charges on DNA, it is relatively easy to separate DNA from a variety of closely related contaminants and it is even possible to separate different types of DNA from each other. These selective adsorption methods have the advantage of providing high purity DNA in a relatively short period of time. However, as the number of applications increase and the demand for faster, cheaper, simpler and more automatable technology increases, the need for better technologies or improvements to existing technologies becomes apparent. In this application, we describe a novel method for purifying DNA that is rapid, simple and highly automatable. This method is based on the observation that DNA, when first contacted with a protonated cation exchange resin and subsequently contacted with a hydroxylated anion exchange resin, does not bind efficiently or, in some cases detectably, to the latter resin. This observation is unexpected, as numerous publications have detailed methods for purification of DNA based on its efficient binding to anion exchange resins. Since many contaminants of DNA reactions bind as expected to ion exchange resins under these conditions, the result is a simple, rapid and highly automatable method for purification of DNA.

SUMMARY OF THE INVENTION

It is an object of the invention to provide a method for purifying DNA in solution from aqueous samples using porous magnetic particles bearing both positive and negative charges on the surfaces of the particle. It is yet another object of the invention to provide a method for preparing particles having properties that are particularly useful for the purification of DNA by the ion exchange method of the invention. Commercially available ion exchange resins are magnetized in the method of the invention by mixing the resin particles with either uncharged or counter-charged magnetic nanoparticles and separating the unbound nanoparticles in a washing process. The magnetized ion exchange resins are then added either sequentially or simultaneously to the DNA-containing sample using an excess of anionic charge-equivalents in the cation exchange resin. The magnetic resins are then separated from the sample by the use of a magnet, leaving purified DNA.

DETAILED DESCRIPTION OF THE INVENTION

In the method of the invention, mixed-bed ion exchange resins can be used to purify DNA in solution by selectively removing contaminants. The contaminants in question are primarily salts, nucleotides and (in PCR reactions) primers. As these are some of the principal contaminants of enzymatic reactions used in the processing and analysis of DNA, this has considerable commercial utility. Examples of reactions that may be purified using this system include sequencing and PCR reactions, as well as a variety of other enzymatic reactions. When the ion exchange resins are used in a batch format and are present in limiting quantities, binding of salts, nucleotides and primers occurs more efficiently than the binding of the DNA of interest. By manipulating the anion exchange resin and by the addition of linear polyacrylamide, products may be developed that function to selectively separate double stranded DNA from short single stranded DNA, salts and nucleotides or to selectively separate single stranded DNA from salts and fluorescently labeled (and unlabeled) nucleotides. Addition of solid phase reagents useful for protein or detergent removal can be used to further purify DNA samples. An example of such a reagent is SOPE resin (Edge BioSystems, Gaithersburg, MD). Other reagents with similar characteristics may also be used.

Prior to use, both the cation exchange resins and the anion exchange resins used in the method of this invention are prepared by washing commercially available resin suspensions with either water, if the resin is available in a suitable form, or with an appropriate acid or base, acid for a cation exchange resin and base for an anion exchange resin. Examples of resins useful in this invention include, AG® MP-1 (BioRad Laboratories, Redmond, Calif.), Dowex® 2×8 (Sigma, St. Louis, Mo.), Amberlite® IRP-64 (Sigma), CM52 (Whatman), MagaCell-CM (Cortex Biochem, San Diego, Calif.), and Amberlite® CG-50 (Sigma). Many other ion exchange resins are available in a variety of sizes, porosities and functional groups and may be empirically screened for suitability of use in the method of the invention. For the purposes of the invention, the cation exchange resin must be in the protonated form and the anion exchange resin must be in the hydroxylated form. Binding of salts and other contaminants to the resin results in the displacement of either the proton or the hydroxyl group from the respective cation or anion exchange resins. Consequently, water is formed as the sample is purified. For some applications, additional washes with solvents or solutions other than acids and bases may be required to remove soluble interfering substances present in commercially available resins, that interfere with downstream processing. For example, in certain cases anion exchange resins to be used for clean up of sequencing reactions should be washed with polar solvent to remove substances that interfere with chromatographic separation of the product. By way of example, but without limitation, useful polar solvents for this cleanup procedure include methanol, ethanol and isopropanol. The preferred solvent is ethanol. Washing is performed in column or batch formats according to standard methods. The preferred format is the column format. A typical washing procedure for preparation of Dowex 2×8 400 anion exchange resin is described in example 1. This example is provided for purposes of illustration and should not be construed as limiting the invention. These procedures are well known to those of skill in the art and many variations on this process can be used to yield a resin fully substituted with the appropriate counterion and substantially free of soluble, interfering contaminants. Suitable acids or acidic buffers for washing the cation exchange resin include acetic acid, hydrochloric acid and sodium acetate buffers. The preferred acid for preparation of the cation exchange resin is hydrochloric. The preferred base for preparation of anion exchange resin is sodium hydroxide. The latter is a typical base used to wash anion exchange resins, and other bases may be used as are known to those of skill in the art. The extent of washing required to provide a suitable resin is a function of the resin, the washing procedure (column or batch) and the initial purity of the commercially supplied material. The suitability of any particular washing procedure as known to those of skill in the art can be readily determined empirically. The endpoint of any such washing procedure is a resin that is fully substituted with the appropriate counterion and substantially free of soluble contaminants that interfere with downstream applications of the DNA purified by the method of the invention. For use in the invention, the purified resins are used as a settled bed (no excess of water over resin) or diluted up to 4:1 v/v and optimally 1.5:1 v/v with water or with 3–6%, and optimally 5%, linear polyacrylamide. The linear polyacrylamide is used as a suspending agent and as an active ingredient in the resin suspension. The size of the resins that may be used in the method of the invention is between 1 and 300 microns and is optimally between 25 and 75 microns.

Some ion exchange resins are commercially available as micron-sized magnetic particles. Magnetic particles are particularly useful in the automated solid phase is separations currently common in the biotechnology industry. However, these resins tend to be expensive and many useful commercial ion exchange resins are not readily available in magnetic form. The latter resins may be magnetized for use in the method of the invention by the procedure described below using ferrous nanoparticles. This method has utility for ion exchange resins primarily in the 25–300 microns size. The ferrous nanoparticles of the invention can be obtained commercially or may be synthesized according to published methods (Enzel, P., et al., J. Chem. Educ." 76: 943–949, July 1999). For the purposes of the examples provided herein, anionic ferrous nanoparticles (cat no. EMG707), cationic ferrous nanoparticles (cat no. EMG605) and uncharged ferrous nanoparticles (cat no. EMG1111) were obtained in aqueous colloidal suspensions from Ferrofluidics Corporation, Nashua, NH. The ferrofluids were used as obtained from the manufacturer and optimally diluted, 1:15–1:20 with ion exchange resin suspension in water. The range of useful dilutions is 1:5–1:50. After mixing, the ferrofluid/ion exchange resin mix was washed with water until no visible magnetic particles were released into the supernatant. Washing may be successfully performed by a number of different procedures including by way of example, but without limitation, centrifugation, filtration, gravitational settling and magnetic attraction. The final resin suspension was used either as a settled bed or diluted up to 5:1 v/v and optimally 1.5:1 v/v with water or with 3–6%, and optimally 5%, linear polyacrylamide. Macroreticular resins are more readily magnetized in this procedure than microporous resins. Anion exchange resins may be magnetized with anionic ferrous nanoparticles, or uncharged ferrous nanoparticles. Cation exchange resins may be magnetized with cationic ferrous nanoparticles. A detailed procedure for the magnetization of Dowex® 2×8-400 resin is provided in example 2. This example is provided for purposes of illustration and should not be construed as limiting.

In the method of the invention, DNA is purified by adding the cation exchange resin suspension and the anion exchange resin either sequentially with the cation exchange resin first, or simultaneously to the DNA-containing sample using an amount of cation exchange resin that is equal to or greater than the amount of anion exchange resin as measured by charge equivalents. After mixing and incubation at room temperature, the purified sample is separated from the resins by centrifugation, filtration, magnetic attraction (with magnetized resins) or other means known to those of skill in the art for separating particulates from soluble materials. The soluble fraction that remains contains purified DNA. Linear polyacrylamide is not a necessary ingredient of the resin suspension for purification of single stranded DNA, but is necessary for purification of samples containing double stranded DNA.

The types of DNA that may be purified by this method include single stranded DNA, and both linear and supercoiled double stranded DNA. It may be used to purify DNA from aqueous solutions such as enzymatic reactions and cleared lysates. By controlling the amount of resin, type of resin, length of exposure to the resin, and the amount of linear polyacrylamide, DNA binding to the anion exchange resin can be minimized or blocked, without affecting the binding of salts, nucleotides and primers. As stated previously, the order of addition is an important variable. The cation exchange resin must be added simultaneously with or prior to the addition of the anion exchange resin. If the cation exchange resin is added before the anion exchange resin, less of both resins are required. In addition, if the DNA is double stranded, it will be denatured if the anion exchange resin is added first. The optimal time of incubation and amount of resin added are also linked. The more resin added, the less the time required to obtain a purified sample. The optimal quantity of resin added and the relative amounts of cation and anion exchange resin are determined empirically by systematically varying these amounts. By way of example, but without limitation, 20 ul of mixed resin suspension is required for purification of DNA from 10 ul sequencing reactions, with an incubation time of 3 minutes. Decreasing the amount of resin suspension to 10 ul increases required incubation time to 5 minutes. The range of useful quantities and ratios also varies according to the type of sample being purified. For situations in which the cation exchange resin is diluted in 5% linear polyacrylamide, and the resins are pre-mixed and added simultaneously, up to 10-fold excess of cation exchange resin may be used with 2.3-fold excess optimal for purification of sequencing reactions and 1.1-fold excess optimal for purification of PCR and other enzymatic reactions. In this same situation, the amount of anion exchange resin added for purification of sequencing reactions ranges from 200 u equivalents/ml to 1600 u eq/ml of sequencing reaction buffer and optimally 400–800 u eq/ml, for 5 minutes and 3 minutes of contact time respectively. The amount of anion exchange resin added for purification of PCR reactions is 20–200 u eq/ml of PCR reaction buffer and is optimally 35–80 u eq/ml, for 5 minutes and 3 minutes, of contact time respectively. Larger quantities of ion exchange resin may be used, but have limited utility due to the sample dilution resulting from the use of such quantities. The total volume of resin suspension added for purification of sequencing reactions with a minimum contact time of five minutes is equal to the volume of the sequencing reaction (e.g. 10 ul resin suspension for every 10 ul sequencing reaction). Contact time may be reduced to 3 minutes by doubling the resin volume with a concomitant dilution of product. Doubling the amount of resin again can further reduce the minimum contact time between resin suspension and sample, but the sample dilution factor becomes sufficiently large that it has limited utility in commercial applications. For purposes of illustration, the purification of sequencing reactions and PCR reactions are described in examples 3 and 4. These examples are provided for illustration purposes only and should not be construed as limiting the invention in any way. Example 3 describes use of the method to purify a sequencing reaction where the resins are combined prior to the purification process. Example 4 illustrates the use of the method to purify a PCR reaction using step-wise addition of cation exchange and anion exchange resins.

Also illustrated in example 4 is the effect of linear polyacrylamide on the recovery of DNA from PCR reactions. In this example, in the absence of linear polyacrylamide, DNA binding to the resin is greater than 90%. Addition of polyacrylamide (3% final concentration in the cation exchange resin; 0.86% in the resin mix) blocks the DNA binding. The extensive binding of DNA to the resin suspension is not observed with sequencing reaction products. This is presumably a reflection of the differences in charge density between the single stranded DNA product of the sequencing reaction and the double stranded DNA product of the PCR reaction. The optimal anion exchange resin for purification of PCR reactions is AG® MP-1 (BioRad Laboratories).

EXAMPLE 1

Washing of Dowex 2x8 400

400 g Dowex 2x8-400 was suspended in 350 ml deionized $H_2O$, settled for 30 minutes and the supernatant was aspirated to remove fine particles. 150 ml deionized $H_2O$ was then added to the resin and the resulting mix was stirred to form a slurry, and added to a 5.0x60 cm column with a plunger, a feeding tube at the bottom of the column and a waste tube at the top. After the resin settled for 16 hours, the liquid flow rate was set at 37 ml/min and the following was pumped through the column: 1 liter of deionized $H_2O$, 2.5 liters of 100% ethanol, 1.5 liters of deionized $H_2O$, 5 liters of 1N NaOH, and 6 liters deionized $H_2O$. If the pH of the eluate was higher than 6.5, additional washes with 0.5 liters of deionized $H_2O$ were done until the pH was lower than 6.5.

EXAMPLE 2

Magnetization of Dowex 2x8 400

To magnetize Dowex 2x8-400, 33 ml of Ferrofluid EMG 707 (Ferrofluidics, Nashua, N.H.) previously sonicated in an ultrasound water bath for 20 minutes was added to 500 ml washed resin suspended in a minimum of water (settled bed). The resulting mix was stirred thoroughly using a spatula and incubated at room temperature for 10 minutes, followed by nine washes with 3.5 liters of deionized $H_2O$.

EXAMPLE 3

Purification of a Sequencing Reaction

A sequencing reaction containing 1 μl of Big-Dye™ mix (Applied BioSystems, Foster City, Calif.), 1 μl of 200 ng/μl pEAK10 plasmid (Edge BioSystems), 1 μl of 3.2 μM PEAK8 reverse primer (Edge BioSystems) and 2 μl deionized $H_2O$, was cycled 35 times on a thermocycler at 96° C. for 30 seconds, 50° C. for 15 seconds and 60° C. for 4 minutes. Upon completion of the reaction 10 μl of magnetized mixed bed ion exchange resin (6.6 μl of 40% slurry of magnetized Amberlite IRP-64 in 3% linear polyacrylamide mixed with 3.3 μl settled bed of Dowex® 2x8–400 washed and magnetized as detailed in examples 1 and 2) was added to the sample in a 1.5 ml microcentrifuge tube and mixed for 3 minutes in a Vortex Genie-2 mixer at speed Vortex-3. The microtube tube was inserted in a tube magnet (Promega Corp, Madison, Wis.) and 40 μl deionized $H_2O$ were added. After 30 seconds 15 μl of supernatant were transferred to a fresh tube and injected in an ABI/Prism 3700 Sequencer. The resulting output showed the sample to be free of unincorporated dyes, with good signal strength. The first sequence error beyond base 20 was noted at base 758. The signal strength and accuracy results obtained with this method are typical or slightly better than the results obtained with other purification systems.

EXAMPLE 4

Effect of Linear Polyacrylamide on PCR Product Purification

In this experiment, 10 μl PCR reactions containing 7 μl of 40 ng/μl pEAK10-GFP plasmid (Edge BioSystems), 7 μl of 100 ng/μl PEAK8 forward primer (Edge BioSystems), 7 μl of 100 ng/μl PEAK8 reverse primer (Edge BioSystems), 35 μl of 10x Taq buffer (Life Technologies), 10.5 μl of 50 mM $MgCl_2$, 1.75 μl of Taq polymerase (5 U/μl, Life Technologies), 35 μl of 2.5 mM dNTPs mix, and 247 μl deionized $H_2O$ were cycled 25 times at 94° C. for 1 minute, 54° C. for 1 minute and 72° C. for 1 minute PTC100 thermocycler (MJ Research, Waltham, Mass.). In most samples, the completed reaction was mixed with 1 μl of a random 18-nucleotide primer solution (1 μg/μl) to permit visualization of primer removal on an agarose gel. The samples were purified by adding 2 μl (40% slurry) of magnetized Amberlite IRP-64 (Sigma) cation exchange resin resuspended in either 5% linear polyacrylamide or water and mixing for 10 seconds in a Vortex-Genie 2 at speed Vortex-3.5 μl of magnetized AG® MP-1 (BioRad Laboratories) anion exchange resin (50% slurry) was then added and mixed for an additional 5 minutes in a Vortex Genie-2 at speed Vortex-3. These conditions have been shown in conductivity studies to removal all detectable salt. The samples were then inserted in a microtube magnet device (Promega Corp, Madison, Wis.) and the particle-free supernatants were electrophoresed on a 1% agarose gel along with non-purified PCR reactionlprimer mix. In the absence of linear polyacrylamide, PCR product was barely detectable by gel. In the presence of linear polyacrylamide, no detectable loss could be observed on the gel relative to the untreated control. In all cases, no primer was observed.

| Cation exchanger | Amplicon recovery | Primer removal |
| --- | --- | --- |
| In diH$_2$O | ≤5% | ≥95% |
| In linear polyacrylamide | ≥70% | ≥95% |

What is claimed is:

1. A method for purification of single-stranded DNA in aqueous solution comprising:
   contacting the single-stranded DNA in aqueous solution with a resin suspension comprising a porous cation exchange resin and a porous anion exchange resin; and
   removing the resin suspension from the single-stranded DNA in aqueous solution.

2. A method for purification of single-stranded DNA in aqueous solution comprising:
   contacting the single-stranded DNA solution with a first resin suspension comprising a porous cation exchange resin, then contacting the solution with a second resin suspension comprising porous anion exchange resin; and
   removing the first and the second resin suspensions from the single-stranded DNA in aqueous solution.

3. A method for purification of DNA in aqueous solution comprising:
   contacting the DNA in aqueous solution with a resin suspension comprising a porous cation exchange resin, a porous anion exchange resin, and linear polyacrylamide; and
   removing the resin suspension from the DNA in aqueous solution.

4. A method for purification of DNA in aqueous solution comprising:
   contacting the DNA in aqueous solution with a first resin suspension comprising a porous cation exchange resin, then contacting the solution with a second resin suspension comprising a porous anion exchange resin, wherein either or both of the first and the second resin suspensions further comprise linear polyacrylamide; and
   removing the first and the second resin suspensions from the DNA in aqueous solution.

5. The method of claim 1 wherein the porous cation exchange resin and the porous anion exchange resin are magnetic.

6. The method of claim 2 wherein the porous cation exchange resin and the porous anion exchange resin are magnetic.

7. The method of claim 3 wherein the porous cation exchange resin and the porous anion exchange resin are magnetic.

8. The method of claim 4 wherein the porous cation exchange resin and the porous anion exchange resin are magnetic.

9. The method of claim 5 wherein the step of removing is performed with a magnet.

10. The method of claim 6 wherein the step of removing is performed with a magnet.

11. The method of claim 7 wherein the step of removing is performed with a magnet.

12. The method of claim 8 wherein the step of removing is performed with a magnet.

13. The method of claim 1 wherein the aqueous solution is a cleared lysate.

14. The method of claim 2 wherein the aqueous solution is a cleared lysate.

15. The method of claim 3 wherein the aqueous solution is a cleared lysate.

16. The method of claim 4 wherein the aqueous solution is a cleared lysate.

17. The method of claim 1 wherein the aqueous solution is an enzymatic reaction.

18. The method of claim 2 wherein the aqueous solution is an enzymatic reaction.

19. The method of claim 3 wherein the aqueous solution is an enzymatic reaction.

20. The method of claim 4 wherein the aqueous solution is an enzymatic reaction.

21. The method of claim 17 wherein the enzymatic reaction is a sequencing reaction.

22. The method of claim 18 wherein the enzymatic reaction is a sequencing reaction.

23. The method of claim 19 wherein the enzymatic reaction is a sequencing reaction.

24. The method of claim 20 wherein the enzymatic reaction is a sequencing reaction.

25. The method of claim 19 wherein the enzymatic reaction is a PCR reaction.

26. The method of claim 20 wherein the enzymatic reaction is a PCR reaction.

* * * * *

UNITED STATES PATENT AND TRADEMARK OFFICE
CERTIFICATE OF CORRECTION

PATENT NO.    : 6,504,021 B1
DATED         : January 7, 2003
INVENTOR(S)   : Eva Kristyanne et al.

It is certified that error appears in the above-identified patent and that said Letters Patent is hereby corrected as shown below:

<u>Title page,</u>
Item [56], References Cited, U.S. PATENT DOCUMENTS,

-- 6,414,136     07/2002     Spicer et al. -- as been inserted.

Signed and Sealed this

Seventeenth Day of June, 2003

JAMES E. ROGAN
*Director of the United States Patent and Trademark Office*